(12) United States Patent
Yuan et al.

(10) Patent No.: US 11,028,356 B2
(45) Date of Patent: Jun. 8, 2021

(54) CELL CULTURE APPARATUS AND METHOD

(71) Applicant: Guangzhou Jet Bio-Filtration Co., Ltd., Guangzhou (CN)

(72) Inventors: Jianhua Yuan, Guangzhou (CN); Huilun Li, Guangzhou (CN); Wenjiang Wang, Guangzhou (CN); Jialiang Su, Guangzhou (CN); Xiaolin Li, Guangzhou (CN); Yong Chen, Guangzhou (CN)

(73) Assignee: GUANGZHOU JET BIO-FILTRATION CO., LTD., Guangzhou (CN)

( * ) Notice: Subject to any disclaimer, the term of this patent is extended or adjusted under 35 U.S.C. 154(b) by 210 days.

(21) Appl. No.: 16/079,407

(22) PCT Filed: Mar. 30, 2016

(86) PCT No.: PCT/CN2016/077848
§ 371 (c)(1),
(2) Date: Aug. 23, 2018

(87) PCT Pub. No.: WO2017/143640
PCT Pub. Date: Aug. 31, 2017

(65) Prior Publication Data
US 2019/0010437 A1    Jan. 10, 2019

(30) Foreign Application Priority Data
Feb. 26, 2016    (CN) .......................... 201610109259.9

(51) Int. Cl.
*C12M 1/12*      (2006.01)
*C12M 1/04*      (2006.01)
(Continued)

(52) U.S. Cl.
CPC ............ *C12M 23/06* (2013.01); *C12M 23/24* (2013.01); *C12M 23/48* (2013.01); *C12M 23/50* (2013.01); *C12M 29/00* (2013.01); *C12M 29/10* (2013.01)

(58) Field of Classification Search
CPC ...... C12M 23/06; C12M 23/24; C12M 23/48; C12M 23/50; C12M 23/38; C12M 23/46;
(Continued)

(56) References Cited

U.S. PATENT DOCUMENTS

| 4,918,019 A * | 4/1990 | Guinn .................... C12M 29/12 |
| | | 435/286.5 |
| 7,122,371 B1 | 10/2006 | Ma |
| 2014/0227769 A1* | 8/2014 | Strobbe ................ C12N 5/0607 |
| | | 435/287.1 |

FOREIGN PATENT DOCUMENTS

| CN | 1168921 A | 12/1997 |
| CN | 1560225 A | 1/2005 |

(Continued)

OTHER PUBLICATIONS

First Office Action for Chinese Counterpart Patent Application No. 201610109259.9, dated Apr. 17, 2017, and brief translation of objections (6 pages).

(Continued)

*Primary Examiner* — Michael L Hobbs
(74) *Attorney, Agent, or Firm* — Kagan Binder, PLLC

(57) ABSTRACT

Provided are cell culture apparatus and method. The cell culture apparatus comprises a culture column and a perfusion system, the culture column comprising a first and a second tube-connecting caps and a support for cells to attach and grow thereon. The first and the second tube-connecting caps are respectively provided with a perfusion inlet and a perfusion outlet; The perfusion system comprises a culture medium storage device, a perfusion tube and a perfusion (Continued)

pump. A complete and closed culture column is formed in the cell culture device after the cells are inoculated, and the culturing is completed by the perfusion system to avoid contamination.

10 Claims, 10 Drawing Sheets

(51) Int. Cl.
  *C12M 1/00* (2006.01)
  *C12M 3/00* (2006.01)

(58) Field of Classification Search
  CPC ...... C12M 23/58; C12M 29/00; C12M 29/10; C12M 29/04; C12M 29/26; C12M 33/00; C12M 37/04
  See application file for complete search history.

(56) References Cited

FOREIGN PATENT DOCUMENTS

| | | | |
|---|---|---|---|
| CN | 101342099 A | 1/2009 | |
| CN | 102719391 A | 10/2012 | |
| CN | 202626198 U | 12/2012 | |
| CN | 103100119 A | 5/2013 | |
| CN | 103243027 A | 8/2013 | |
| CN | 103266182 * | 8/2013 | ............... C12Q 3/00 |
| CN | 103266182 A | 8/2013 | |
| CN | 103396935 A | 11/2013 | |
| CN | 103642685 A | 3/2014 | |
| CN | 103649305 A | 3/2014 | |
| CN | 104619830 A | 5/2015 | |
| CN | 204550625 U | 8/2015 | |
| CN | 205710764 U | 11/2016 | |

OTHER PUBLICATIONS

Second Office Action for Chinese Counterpart Patent Application No. 201610109259.9, dated Nov. 16, 2017, and English translation thereof (7 pages).
LV. Renfa et al., 'The Design of a Circulating-Perfusion Device for 3D Engineered Tissue Cultured in Vitro and Test for its Capability'. Acta Academiae Medicinae Militaris Tertlae. vol. 27. No. I6, Aug. 31, 2005 (Aug. 31, 2005), including English Abstract (4 pages).
First Search Report of Chinese Counterpart CN201610109259.9, and English translation thereof (4 pages).
Supplementary Search Report of Chinese Counterpart CN201610109259.9, and English translation thereof (2 pages).
International Search Report, and English Translation thereof, for International Application No. PCT/CN2016/077848, dated Nov. 30, 2016 (2 pages).
First Search Report of Chinese Counterpart CN201610109259.9 (1 page).
Supplementary Search Report of Chinese Counterpart CN201610109259.9 (1 page).
First Office Action for Chinese Counterpart Patent Application No. 201610109259.9, dated Apr. 17, 2017, (5 pages).
Second Office Action for Chinese Counterpart Patent Application No. 201610109259.9, dated Nov. 16, 2017, (3 pages).
Unpublished Utility U.S. Appl. No. 15/775,695, filed May 11, 2018.
Unpublished Utility U.S. Appl. No. 15/775,678, filed May 11, 2018.

* cited by examiner

CELL CULTURE APPARATUS AND METHOD

TECHNICAL FIELD

The present disclosure relates to the technical field of cell culture, particularly to a cell culture apparatus and method.

BACKGROUND

In recent years, technologies in tissue regeneration engineering, biomedical engineering, and cell therapy industry have developed rapidly. It has become an important direction to produce a large quantity of cells, extracellular secretions, and cell therapy products by large-scale in vitro culture of animal or human cells in current clinical application of cells. For example, in vitro culture of target cells is requested in skin cell culture and new skin acquisition after tissue trauma or burn, tumor cell therapy, cell cosmetology, and cell slimming and the like.

Currently, at home and abroad, cells are cultured in vitro by providing a culture medium and a culture apparatus for the growth of cells in vitro and placing the culture apparatus in an incubator, Commonly used cell culture apparatuses mainly include cell culture plates, culture flasks, culture dishes, culture roller bottles, and larger volume of cell factories in recent years.

However, at present, commercialized cell culture apparatuses, regardless of small size of culture plates, culture dishes, or culture flasks, or larger size of culture roller bottles or cell factories, all are used in an open-type culture; that is, it is necessary to open a lid of the apparatuses for all operations, such as cell inoculation, cell harvest, or replacement of nutrients during culture. The problem of contamination caused by the lid opening operation is the first to be solved.

Moreover, hydrophilic treatment is performed at the bottom of apparatuses, such as the existing culture plates, culture flasks, culture dishes, culture roller bottles, cell factories and the like, so that cells are adhered to the bottom for growth, resulting in a small surface area for adherent culture, and a small amount of cells or cell secretions harvested in a single culture. To harvest more cells or cell secretions, more apparatuses are required or several repeated culture operations are performed in limited amount of apparatuses. Both ways of obtaining a large number of target products have problems such as complicated manipulation, increased workload, also easy contamination, and the like.

Moreover, the cells in the existing culture plates, culture flasks, culture dishes, culture roller bottles, and cell factories will be chemically or physically damaged when harvested by chemical digestion with trypsin or physical scraping with a cell scraper.

SUMMARY

Based on this, for the above problem, it is necessary to provide a cell culture apparatus. Using the cell culture apparatus, cells may be cultured in a closed-type way, thereby avoiding the problem of contamination that may be raised by open-type culture; by using a scaffold, the cell culture apparatus further provides more surface area for cell growth in the culture apparatus, achieving the purpose of large-scale cell culture.

A cell culture apparatus comprises:

a culture column including a first tube-connecting cover, a second tube-connecting cover and at least a scaffold for adherent growth of cells, the first tube-connecting cover, the at least a scaffold and the second tube-connecting cover being sequentially stacked to for u a culture column having a closed cavity, and the first tube-connecting cover and the second tube-connecting cover each having a perfusion inlet and a perfusion outlet; and a perfusion system including a culture medium storage apparatus, a perfusion tube and a perfusion pump for powering perfusion, the culture medium storage apparatus, the perfusion pump and the perfusion inlet being sequentially communicated via the perfusion tube.

With design of the closed-type culture column in the above cell culture apparatus, only an inoculation process is of open-type during the culture process, and respective components are assembled to form a complete and closed culture column after cell inoculation. During a whole culture period such as during changing the medium for cells and the like, the apparatus will not open again, and the culture is completed by perfusing with the perfusion system, thereby avoiding the possibility of contamination and improving the safety in operation.

In one embodiment, at least two scaffolds are provided, and/or at least two culture columns are provided. By providing a plurality of scaffolds in one culture column, and/or providing a plurality of culture columns in one culture apparatus, more surface area is provided for the cells, and an amount of proliferated cells may be increased by several times or even dozens of times compared to when in a conventional two-dimensional planar culture. It is possible to achieve large-scale cell culture and harvest more cells, secretions, and the like.

In one embodiment, the culture column further includes a sealing ring and a buckle ring having a same number as that of the scaffold, the sealing ring being annular and arranged around an edge of the scaffold, the buckle ring being annular and arranged around an edge of the sealing ring, wherein a buckle ring boss is provided in an inner circumferential side surface of the buckle ring, a buckle ring slot matching the buckle ring boss is provided in an outer circumferential side surface of the sealing ring, and the sealing rings stacked adjacently are in contact with each other. By using the sealing ring matching with the buckle ring not only ensures sealing of the cell culture cavity in the culture column, but also allows conveniently and flexibly selecting a desired number of scaffolds and stackably assembling the respective scaffolds while ensuring a predetermined space between the scaffolds, providing a good environment for cell proliferation.

In one embodiment, the buckle ring is further provided with a fastening hook and a fastening slot, wherein the fastening slot is provided with a fixing lug boss therein, the fastening hook may be inserted into the fastening slot of another buckle ring and fixed to the fixing lug boss of the another buckle ring through a snap-fit, and the sealing, ring, in a stacked contact is pressed and fixed;

the first tube-connecting cover is further provided with a mounting slot, and the fastening hook of the buckle ring adjacent to the first tube-connecting cover may be inserted into the mounting slot and fixed to the first tube-connecting cover through a snap-fit;

the second tube-connecting cover is further provided with a mounting hook, and the mounting hook may be inserted into the fastening slot of the buckle ring adjacent to the second tube-connecting cover and fixed to the fixing lug boss of the buckle ring through a snap-fit.

With the above arrangement, the culture column including a predetermined number of scaffolds can be obtained by flexibly and conveniently assembling with respective buckle rings according to an amount of cells required by different users, enabling more humanization in use.

In one embodiment, the fastening hook and the fastening slot are alternately and evenly arranged around an edge of the buckle ring. The arrangement of both of the fastening hook and the fastening slot on a same buckle ring increases universality of the buckle ring. Meanwhile, the alternate and even arrangement, reduces difficulty for manipulating the buckle ring on one hand, and improves the sealing between the sealing rings on the other hand.

In one embodiment, a scaffold slot adapted to a thickness of a circumferential edge of the scaffold is provided in an inner circumferential side surface of the sealing ring. The sealing ring is mounted on and around the scaffold by snap-fitting the edge of the scaffold into the scaffold slot.

In one embodiment, the scaffold is formed by crisscrossing laminated fibers and a gap for cell adherent growth and circulation of the culture medium is funned between the fibers. The gap is a pore formed between the fibers. The scaffold formed by criss-crossing the fibers can provide more surface area for the cells, further increasing the cell culture scale.

In one embodiment, a surface of the scaffold is grafted with a temperature-sensitive material, and the temperature-sensitive material is subjected to a phase change between hydrophilic phase and hydrophobic phase by changing temperature, so that the cell growing adherently to the scaffold are allowed to achieve temperature-sensitive detachment and harvested after the completion of culture. The grafting treatment of the scaffold can be carried out in a conventional way. The temperature of the temperature-sensitive material may be allowed to lower below its phase transition temperature after the completion of culture, so that objective of automatically detaching the cells from the scaffold is achieved. This avoids a problem that the cells in the existing culture plates, culture flasks, culture dishes, culture roller bottles, and cell factories will be chemically or physically damaged when harvested by chemical digestion with trypsin or physical scraping with a cell scraper.

In one embodiment, the cell culture apparatus further includes a humidification apparatus and an air filter, wherein the humidification apparatus provides humidified gas for the culture medium storage apparatus; and a vent port for the culture medium storage apparatus communicating with external environment is provided with an air filter. Through the above arrangement, the entire cell culture system is isolated from the external environment during a whole cell culture period, avoiding the possibility of contamination by air.

In one embodiment, the cell culture apparatus further includes a fixing bracket and the culture column is mounted on and fixed to the fixing bracket. Moreover, different number of culture columns may be selected and connected in series for the culture according to an amount of cells required by the user, enabling large-scale cell culture and harvesting more cells, secretions, and the like.

The present disclosure further discloses a cell culture method by using the above cell culture apparatus, the method comprising the following steps:

mounting the culture column: providing the first tube-connecting cover, sequentially stacking and mounting a predetermined number of scaffolds on the first tube-connecting cover, inoculating cells to be cultured onto the scaffolds, and then mounting and fixing the second tube-connecting cover on a upper portion of the scaffolds so that the culture column is assembled;

perfusing and culturing cells: communicating the perfusion inlet with the perfusion pump and the culture medium storage apparatus sequentially through the perfusion tube, providing power by the perfusion pump, perfusing a culture medium in the culture medium storage apparatus into the culture column to provide nutrients for cell growth and discharging a metabolite produced by cell metabolism from the perfusion outlet as the culture medium flows.

In the above cell culture method, only an inoculation process is of open-type during the culture process, and respective components are assembled to form a complete and closed culture column after cell inoculation. During a whole culture period such as during changing the medium for cells and the like, the apparatus will not open again, and the culture is completed by perfusing with the perfusion system, thereby avoiding the possibility of contamination and improving the safety in operation.

In one embodiment, with the above cell culture apparatus, and in the step of mounting the culture column:

surrounding and sheathing the scaffold with the sealing ring, and surrounding and sheathing the sealing ring with the buckle ring to form an accessory set, and mounting several accessory sets according to the above method;

providing the first tube-connecting cover, and inserting the fastening hook of the buckle ring in the above-mentioned accessory set into the mounting slot and fixed to the first tube-connecting cover through a snap fit; according to the above method, inserting the fastening hook of the buckle ring in respective accessory set sequentially into the fastening slot of the buckle ring in another accessory set and fixed to the fixing lug boss of the buckle ring in the another accessory set through a snap fit, pressing and fixing the sealing rings in stacked contact, and stacking and mounting a predetermined number of scaffolds sequentially;

inoculating the cells to be cultured onto the above mounted scaffolds;

then, inserting the mounting hook of the second tube-connecting cover into the fastening slot of the buckle ring adjacent to the second tube-connecting cover, and mounting and fixing the second tube-connecting cover so that the culture column is assembled.

With the above arrangement, the culture column including a predetermined number of scaffolds can be obtained by flexibly and conveniently assembling with respective buckle rings according to an amount of cells required by different users, enabling more humanization in use.

Compared with the current technology, the present disclosure has the following beneficial effects:

With design of the closed-type culture column in the cell culture apparatus of the present disclosure, only an inoculation process is of open-type during the culture process, and respective components are assembled to form a complete and closed culture column after cell inoculation. During a whole culture period such as during changing the medium for cells and the like, the apparatus will not open again, and the culture is completed by perfusing with the perfusion system, thereby avoiding the possibility of contamination, improving the safety in operation and so on.

Moreover, by providing the cell culture apparatus with a plurality of scaffolds or a plurality of culture columns, more surface area may be provided in one cell culture apparatus for the cells, and an amount of proliferated cells may be increased by several times or even dozens of times compared to when in a conventional two-dimensional planar culture. It is possible to achieve large-scale cell culture and harvest more cells or secretions.

In the cell culture apparatus, a surface of the scaffolds may be subjected to grafting treatment with the temperature-sensitive material. The temperature of the temperature-sensitive material may be allowed to lower below its phase transition temperature after the completion of culture, so that objective of automatically detaching the cells from the scaffold is achieved. This avoids a problem that the cells in the existing culture plates, culture flasks, culture dishes, culture roller bottles, and cell factories will be chemically or physically damaged when harvested by chemical digestion with trypsin or physical scraping with a cell scraper.

Figure 1:
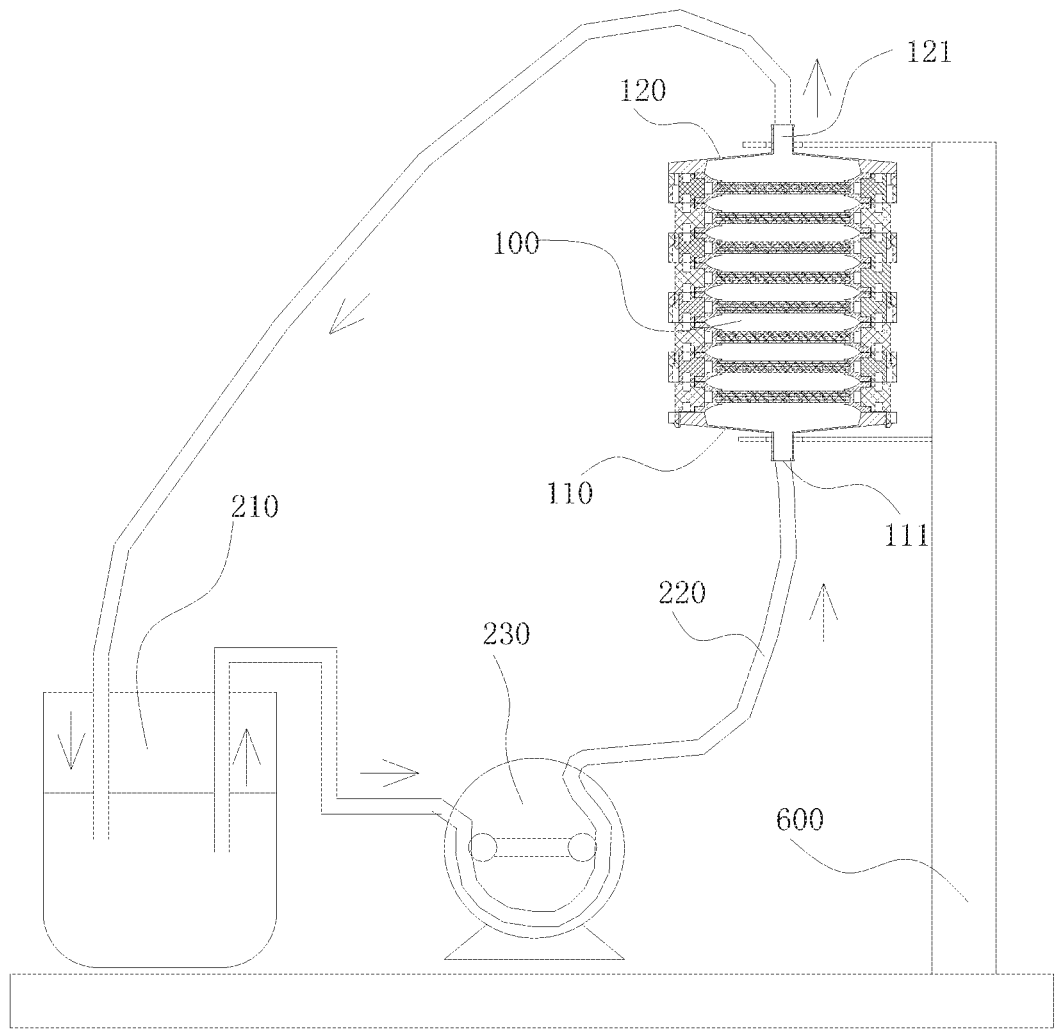
FIG. 1 is a structural schematic diagram of the cell culture apparatus in Example 1.

wherein: 100. a culture column; 110. a first tube-connecting cover; 111. a perfusion inlet; 112. a mounting slot; 120. a second tube-connecting cover; 121, a perfusion outlet; 122. a mounting hook; 130. a scaffold; 140. a sealing ring; 141. a buckle ring slot; 142. a scaffold slot; 150. a buckle ring; 151. a buckle ring boss; 152. a fastening hook; 153. a fastening slot; 154. a fixing lug boss; 210. a culture medium storage apparatus; 220. a perfusion tube; 230. a perfusion pump; 300. a humidification apparatus; 400. an air pump; 500. an air filter; 600. a fixing bracket; 710. a cell harvesting bottle; 720. a cell harvesting tube; 730. a cell harvesting valve; 810. a liquid waste bottle; 820. a liquid waste tube; 830. a liquid waste valve.

DETAILED DESCRIPTION OF THE PREFERRED EMBODIMENTS

Detailed description is set forth hereinafter with reference to the accompanying drawings, in order to fully understand the present disclosure. Preferred embodiments of the present disclosure are shown in the drawings. However, the present disclosure may be implemented in many different ways and is not limited to the embodiments described herein. Rather, these embodiments are provided in order to make the present disclosure more thoroughly and fully understood.

It should be understood that when an element is referred to as "fixed to" another element, it may be directly on the other element or an intervening element may also be present. When an element is considered being "communicated" with another element, it is either directly communicated with the other element or an intervening element may also be present.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

A cell culture apparatus, as shown in FIG. 1, comprises: a culture column 100 and a perfusion system.

The culture column 100 includes a first tube-connecting cover 110, a second tube-connecting cover 120 and at least a scaffold 130 for adherent growth of cells, the first tube-connecting cover 110, the at least a scaffold 130 and the second tube-connecting cover 120 being sequentially stacked to form a culture column 100 having a closed cavity, and die first tube-connecting cover 110 and the second tube-connecting cover 120 each having a perfusion inlet 111 and a perfusion outlet 121.

The perfusion system includes a culture medium storage apparatus 210, a perfusion tube 220 and a perfusion pump 230 for powering perfusion, the culture medium storage apparatus 210, the perfusion pump 230 and the perfusion inlet 111 being sequentially communicated via the perfusion tube 220.

A different number of scaffolds 130 and culture columns 110 may be selected according an amount of cells required by the user. With the above arrangement, more surface area is provided for the cells, and an amount of proliferated cells may be increased by several times or even dozens of times compared to when in a conventional two-dimensional planar culture. It is possible to achieve large-scale cell culture and harvest more cells, secretions and the like.

Figure 2:
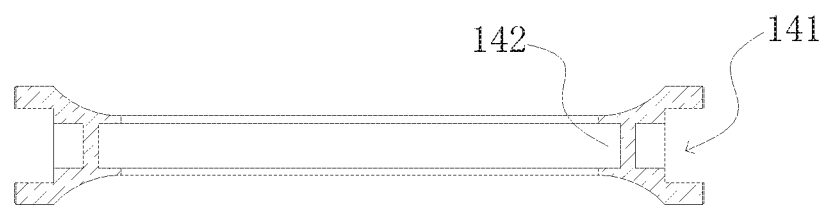
FIG. 2 is a schematic cross-sectional view of a sealing ring.
Figure 3:
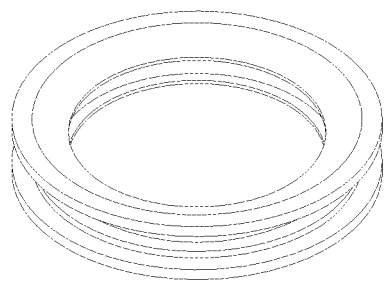
FIG. 3 is a schematic view of a structure and a shape of a sealing ring.
Figure 4:
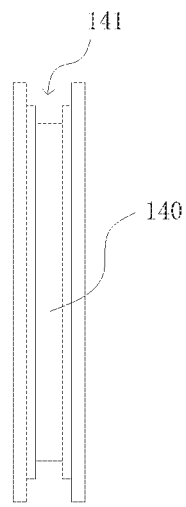
FIG. 4 is a schematic side view of a circumference of a sealing ring.
Figure 12:
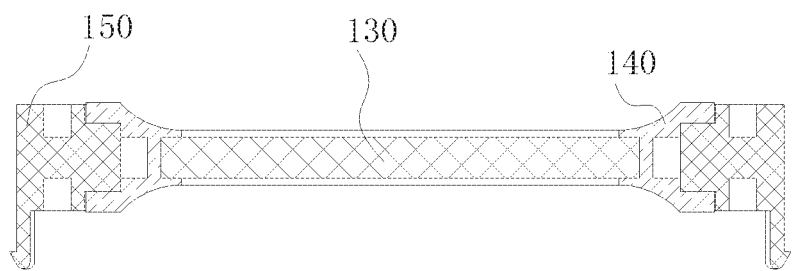
FIG. 12 is a schematic view of matching of a scaffold, a sealing ring and a buckle ring.

Preferably, the culture column 100 further includes a sealing ring 140 and a buckle ring 150 having a same number as that of the scaffold 130; as shown in FIGS. 2-4, the sealing ring 140 being annular and arranged around an edge of the scaffold 130; as shown in FIGS. 5-11, the buckle ring 150 being annular and arranged around an edge of the sealing ring 140, as shown in FIG. 12; wherein a buckle ring boss 151 is provided in an inner circumferential side surface of the buckle ring 150, a buckle ring slot 140 matching the buckle ring boss 151 is provided in an outer circumferential side surface of the sealing ring 140, and the sealing rings 140 stacked adjacently are in contact with each other. It will be appreciated that there are a variety of mounting ways within the culture column, such as the scaffold being mounted within a frame, and the like. However, by a mounting way of matching the sealing rings 140 with the buckle rings 150 not only ensures sealing of the cell culture cavity in the culture column 100, but also allows conveniently and flexibly selecting a desired number of scaffolds and stackably assembling the respective scaffolds while ensuring a predetermined space between the scaffolds, providing a good environment for cell proliferation.

Figure 13:
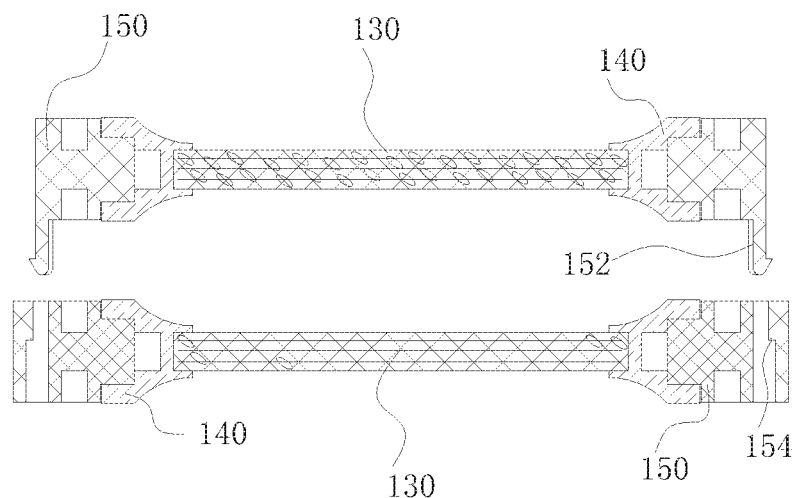
FIG. 13 is a schematic view of matching of a plurality of scaffolds, sealing rings and buckle rings.
Figure 14:
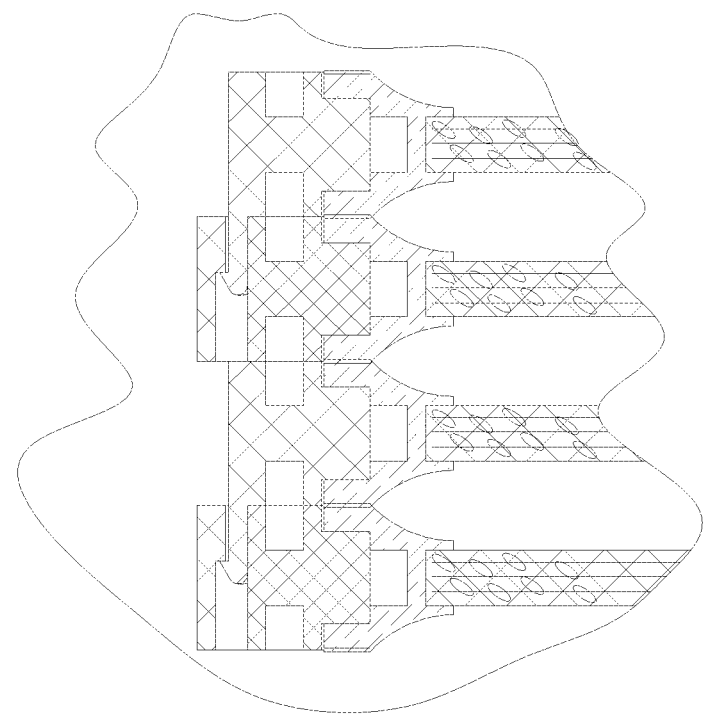
FIG. 14 is a schematic view of mutual matching between buckle rings.

Preferably, as shown in FIG. 13, the buckle ring 150 is further provided with a fastening hook 152 and a fastening slot 153, wherein the fastening slot 153 is provided with a fixing lug boss 154 therein, the fastening hook 152 may be inserted into the fastening slot 153 of another buckle ring and fixed to the fixing lug boss 154 of the another buckle ring through a snap-fit, and the sealing ring 140 in a stacked contact is pressed and fixed, as shown in FIG. 14.

Figure 15:
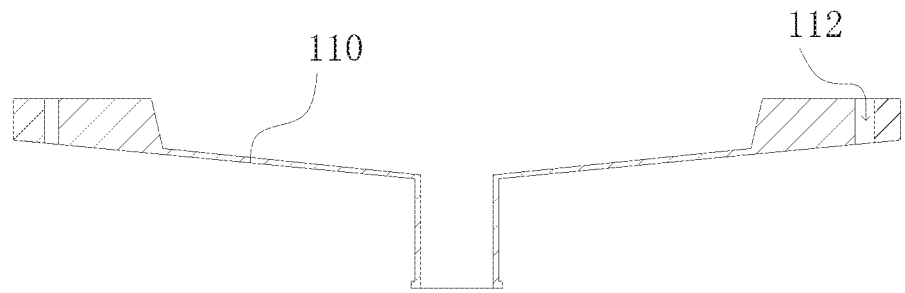
FIG. 15 is a structural schematic view of a first tube-connecting cover.
Figure 16:
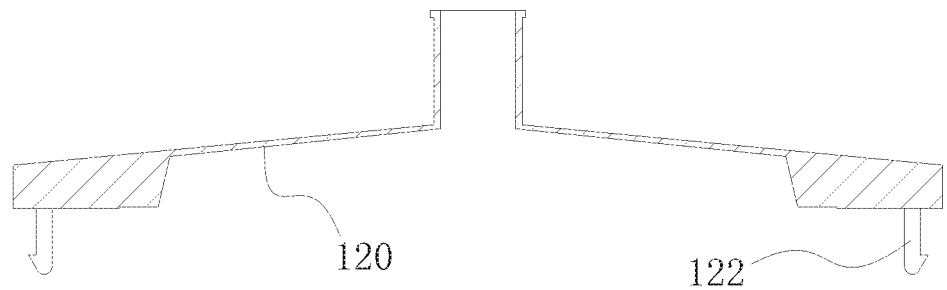
FIG. 16 is a structural schematic view of a second tube-connecting cover.

The first tube-connecting cover 110 is further provided with a mounting slot 112, and the fastening hook of the buckle ring adjacent to the first tube-connecting cover 110 may be inserted into the mounting slot 112 and fixed to the first tube-connecting cover 110 through a snap-fit, as shown in FIG. 15;

The second tube-connecting cover 120 is further provided with a mounting hook 122, and the mounting hook 122 may be inserted into the fastening slot 153 of the buckle ring adjacent to the second tube-connecting cover and fixed to the fixing lug boss 154 of the buckle ring through a snap-fit, as shown in FIG. 16.

It can be understood that the first tube-connecting cover, the second tube-connecting cover and the buckle ring may be mounted and fixed in other ways such as being fixed by a bolt and the like. However, with the above arrangement, the culture column including a predetermined number of scaffolds can be obtained by flexibly and conveniently assembling with respective buckle rings according to an amount of cells required by different users, enabling more humanization in use.

Preferably, the fastening hooks 152 and the fastening slots 153 are alternately and evenly arranged around an edge of the buckle rings 150. It can be understood that an asymmetric design can also be used as long as the sealing of the culture column can be ensured after the fastening hook and the fastening slot have been mounted and fixed. However, the arrangement of both of the fastening hook and the fastening slot on a same buckle ring increases universality of the buckle ring. Meanwhile, the alternate and even arrangement, reduces difficulty for manipulating the buckle ring on one hand, and improves the sealing between the scaling rings on the other hand.

Preferably, a scaffold slot 142 adapted to a thickness of a circumferential edge of the scaffold 130 is provided in an inner circumferential side surface of the sealing ring 140. It can be understood that the sealing ring can also be mounted on the edge of the scaffold in other ways. However, the mounting way of snap-fitting the edge of the scaffold into the scaffold slot has advantages of stability and firmness.

Figure 17:
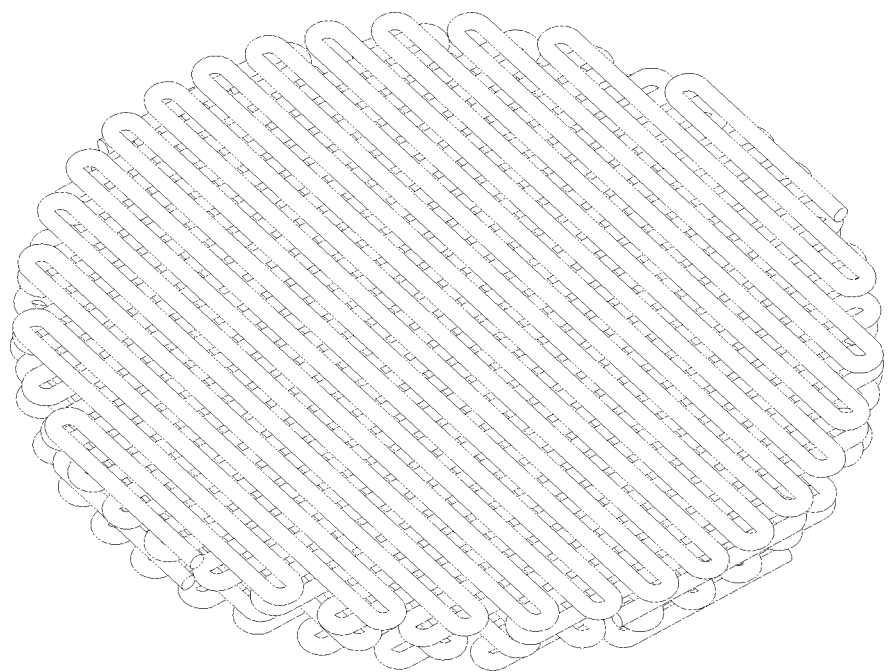
FIG. 17 is a structural schematic view of a scaffold.

Preferably, the scaffold 130 is formed by criss-crossing laminated fibers. As shown in FIG. 17, a gap for cell adherent growth and circulation of the culture medium is formed between the fibers. The gap is a pore formed between the fibers. It can be understood that the scaffold can be manufactured in other ways as long as the pore is retained for circulation of the culture medium. However, the scaffold formed by criss-crossing the fibers can provide more surface area for the cells, further increasing the cell culture scale.

Currently, in cell culture, several materials, such as PS (polystyrene), composition of PS and PCL (polycaprolactone), PLGA (polylactic acid-glycolic acid copolymer), and the like, are commonly used as material of the above scaffold formed by the fibers. The scaffold can be manufactured by conventional injection molding or by an emerging 3D printing method.

Preferably, a surface of the scaffold is grafted with a temperature-sensitive material, and the temperature-sensitive material is subjected to a phase change between hydrophilic phase and hydrophobic phase by changing temperature, so that the cell growing adherently to the scaffold are allowed to achieve temperature-sensitive detachment and harvested after the completion of culture. The grafting treatment of the scaffold can be carried out in a conventional way. The temperature of the temperature-sensitive material may be allowed to lower below its phase transition temperature after the completion of culture, so that objective of automatically detaching the cells from the scaffold is achieved. Considering that a temperature suitable for cell culture is about 37° C. and a critical phase transition temperature of the temperature-sensitive material is preferably 32° C., the cells grows adherently to the wall at a temperature of 37° C., and an optimum detachment temperature in the experiment is about 20° C. It will be understood that the optimum detachment temperature in a specific application can be set depending on different types of cells being cultured and the temperature-sensitive material selected.

Furthermore, it can be understood that the surface of the scaffold may be not subjected to the grafting treatment with the temperature-sensitive material, which does not affect the cell culture effect of the apparatus; however, chemical digestion with trypsin or physical scraping with a cell scraper will be adopted only when the cells are harvested and may cause chemical or physical damage to the cells.

Preferably, the cell culture apparatus further includes a humidification apparatus 300 and an air filter 500, wherein the humidification apparatus 300 provides humidified gas for the culture medium storage apparatus 210; and a vent port for the culture medium storage apparatus 210 communicating with external environment is provided with an air filter 500. Through the above arrangement, the entire cell culture system is isolated from the external environment during the whole cell culture period, avoiding the possibility of contamination by air.

Figure 22:
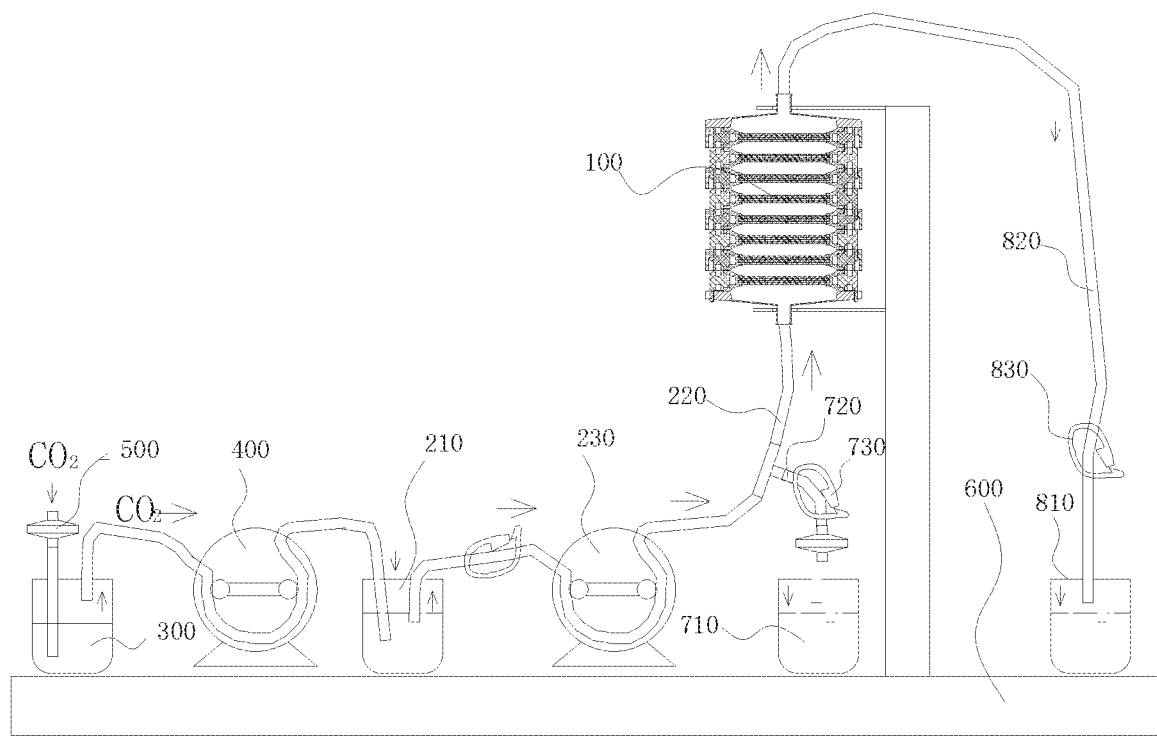
FIG. 22 is a second structural schematic view of the cell culture apparatus in Example 2.

It can be understood that, as shown in FIG. 22, the cell culture apparatus may further include an air pump 400, and the humidification apparatus 300, the air pump 400, and the culture medium storage apparatus 210 are sequentially communicated through a gas tube, and the vent port of the humidification apparatus 300 and the culture medium storage apparatus 210 communicating with the external environment is provided with an air filter 500.

Preferably, the cell culture apparatus further includes a fixing bracket 600, and the culture column 100 is mounted on and fixed to the fixing bracket 600. It can be understood that the user can also place the culture column according to specific requirements.

Example 1

A cell culture apparatus, as shown in FIG. 1, includes: a culture column 100 and a perfusion system.

The culture column 100 includes a first tube-connecting cover 100, a second tube-connecting cover 120, eight scaffolds 130 for cell adherent growth, eight sealing rings 140 and eight buckle rings 150. The first tube-connecting cover 110, the scaffolds 130 and the second tube-connecting cover 120 are sequentially stacked to form a culture column 100 having a closed cavity, the first tube-connecting cover 110 and the second tube-connecting cover 120 each have a perfusion inlet and a perfusion outlet.

Figure 9:
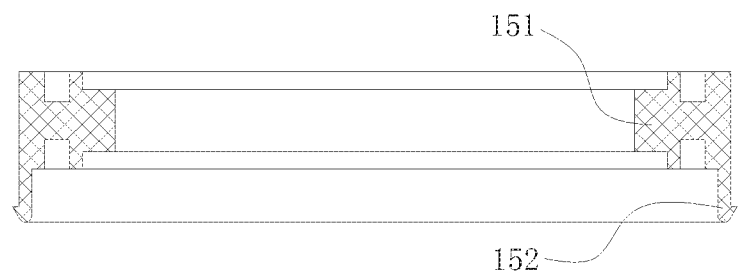
FIG. 9 is a cross-sectional view taken along facet c-c of FIG. 7.
Figure 10:
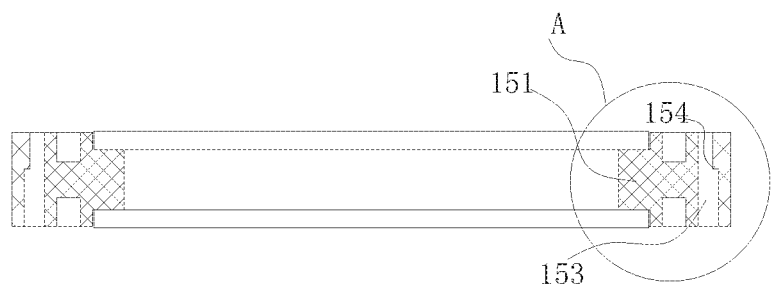
FIG. 10 is a cross-sectional view taken along facet d-d of FIG. 7.
Figure 11:
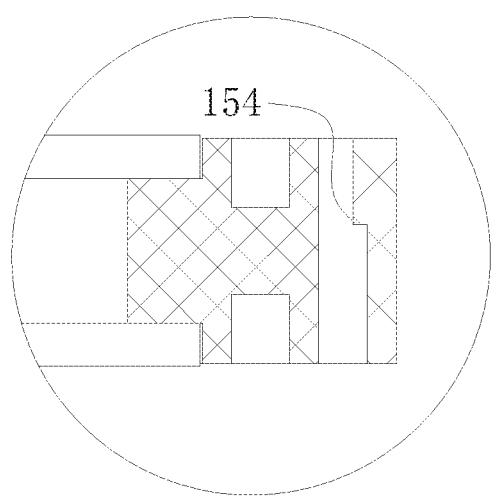
FIG. 11 is a partial enlarged view of portion A of FIG. 10.

The first tube-connecting cover 110, the scaffolds 130 and the second tube-connecting cover 120 are stacked and mounted sequentially in following specific way:

As shown in FIGS. 2-4, the sealing ring 140 is annular and arranged around an edge of the scaffold 130; as shown in FIGS. 5-11, the buckle ring 150 is annular and arranged around an edge of the sealing ring 140, as shown in FIG. 12; a buckle ring boss 151 is provided in an inner circumferential side surface of the buckle ring 150, a buckle ring slot 141 matching the buckle ring boss 151 is provided in an outer circumferential side surface of the sealing ring 140, as shown in FIGS. 4 and 9; and the sealing rings 140 stacked adjacently are in contact with each other.

Figure 18:
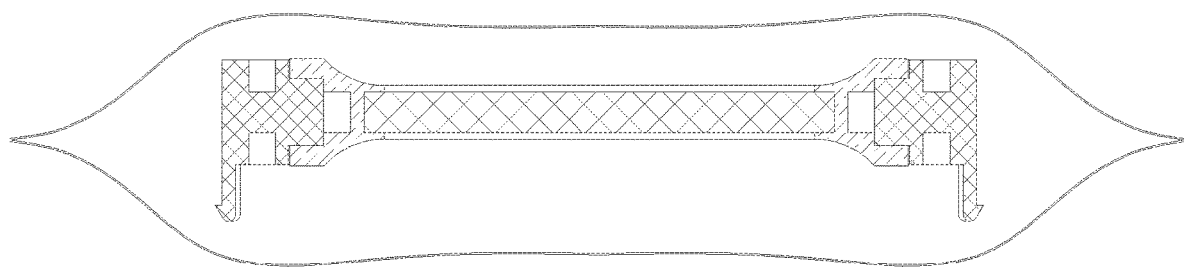
FIG. 18 is a schematic view of a packaging accessory set of a scaffold, a sealing ring and a buckle ring.

Moreover, one scaffold, one sealing ring and one buckle ring can be assembled to form a separately packaged accessory set, as shown in FIG. 18.

In this example, the buckle ring 150 is further provided with a fastening hook 152 and a fastening slot 153. The fastening slot 153 is provided with a fixing lug boss 154 therein, the fastening hook 152 may be inserted into the fastening slot 153 of another buckle ring 150 and fixed to the fixing lug boss 154 of the another buckle ring through a snap-fit, and the sealing ring 140 in a stacked contact is pressed and fixed, as shown in FIGS. 13 and 14;

The first tube-connecting cover 110 is further provided with a mounting slot 112, and the fastening hook 152 of the buckle ring 150 adjacent to the first tube-connecting cover 110 may pass through the mounting slot 112 and may be fixed to the first tube-connecting cover 110 through a snap-fit, as shown in FIG. 15;

The second tube-connecting cover 120 is further provided with a mounting hook 122, and the mounting hook 122 may be inserted into the fastening slot 153 of the buckle ring 150 adjacent to the second tube-connecting cover 120 and fixed to the fixing lug boss 154 of the buckle ring 150 through a snap-fit, as shown in FIG. 16.

Figure 5:
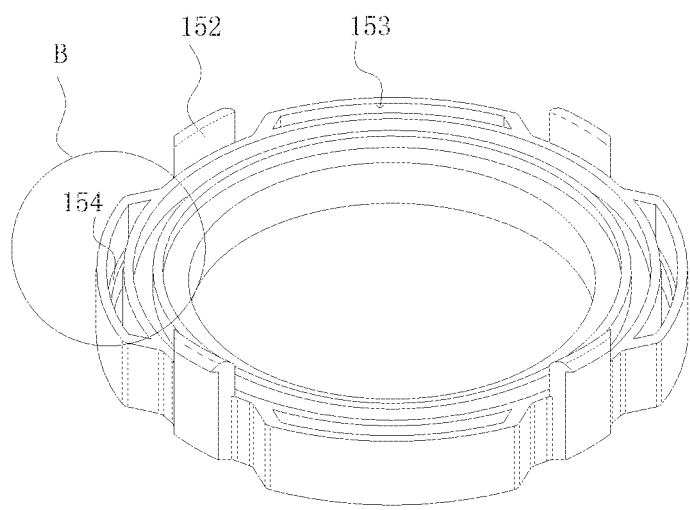
FIG. 5 is a schematic view of a structure and a shape of a buckle ring.
Figure 6:
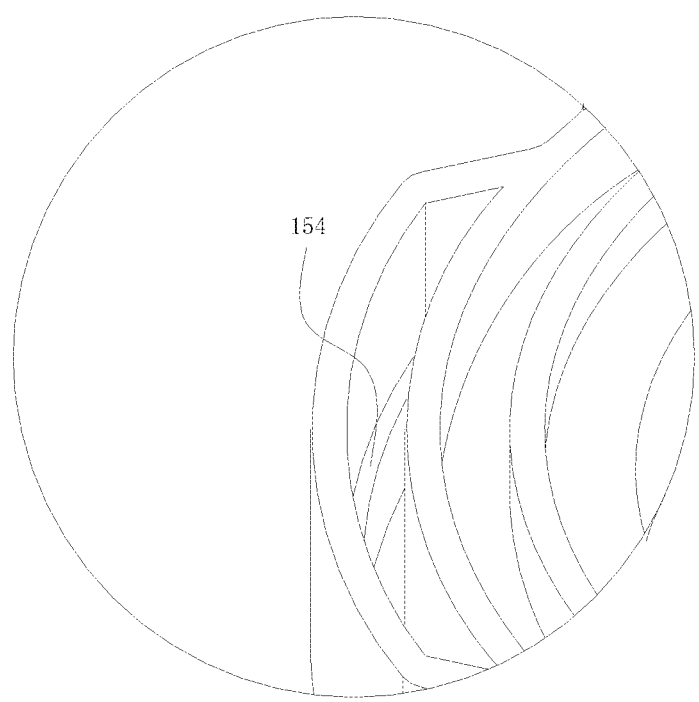
FIG. 6 is a partial enlarged view of portion B of FIG. 5.
Figure 7:
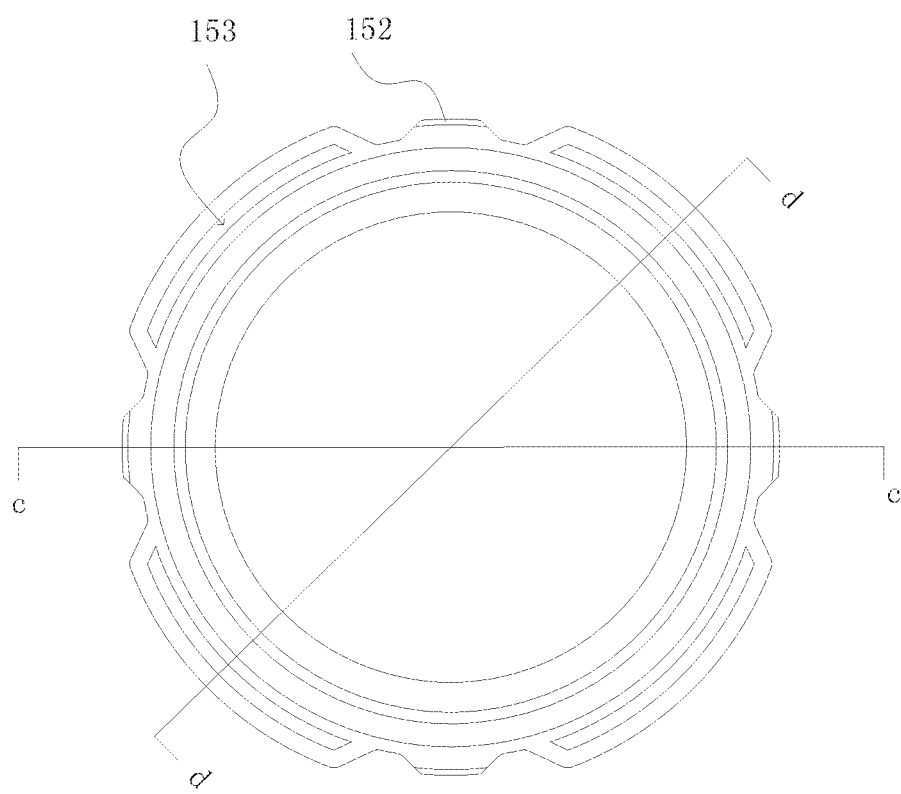
FIG. 7 is a schematic top view of a buckle ring.
Figure 8:
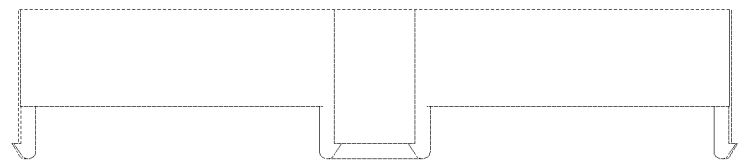
FIG. 8 is a schematic side view of a buckle ring.

In this example, as shown in FIGS. 5 and 7, the fastening hooks 152 and the fastening slots 153 are alternately and evenly arranged around an edge of the buckle ring 150 and can be corresponded interchangeably by rotating an angle of the buckle ring 150, and adjacent buckle rings overlap in such a manner that the fastening hook corresponds to the fastening slot. Moreover, a scaffold slot adapted to a thickness of a circumferential edge of the scaffold is provided in an inner circumferential side surface of the sealing ring.

In this example, the scaffold 130 is formed by crisscrossing laminated fibers. As shown in FIG. 17, a gap for cell adherent growth and circulation of the culture medium is formed between the fibers. The gap is a pore formed between the fibers.

Currently, in cell culture, several materials, such as PS (polystyrene), PS and PCL (polycaprolactone), PLEA (polylactic acid-glycolic acid copolymer), and the like, are commonly used as material of the above scaffold formed by the fibers. The scaffold call be manufactured by conventional injection molding or by an emerging 3D printing method. In this example, a commonly used single fiber filament has a diameter of 400 µm, and the scaffold formed by crisscrossing a plurality of the fibers filaments has three pore size specifications of 300 µm, 400 µm, and 500 µm.

In addition, a surface of the scaffold is grafted with a temperature-sensitive material, and the temperature-sensitive material is subjected to a phase change between hydrophilic; phase and hydrophobic phase by changing temperature, so that the cell growing adherently to the scaffold are allowed to achieve temperature-sensitive detachment and harvested after the completion of culture. The grafting treatment of the scaffold can be carried out in a conventional way. The temperature of the temperature-sensitive material may be allowed to lower below its phase transition temperature after the completion of culture, so that objective of automatically detaching the cells from the scaffold is achieved. Considering that a temperature suitable for cell culture is about 37° C. and a critical phase transition temperature of the temperature-sensitive material is preferably 32° C., the cells grows adherently to the wall at a temperature of 37° C., and an optimum detachment temperature in the experiment is about 20° C.

As shown in FIG. 1, the perfusion system includes a culture medium storage apparatus 210, a perfusion tube 220 and a perfusion pump 230 for powering perfusion, the culture medium storage apparatus 210, the perfusion pump 230 and the perfusion inlet 111 being sequentially communicated via the perfusion tube 220.

In this example, the cell culture apparatus further includes a fixing bracket 600, and the culture column 100 is mounted on and fixed to the fixing bracket 600.

A method for cell culture by using the above cell culture apparatus comprises the following steps:

1. Mounting the Culture Column.

Figure 19:
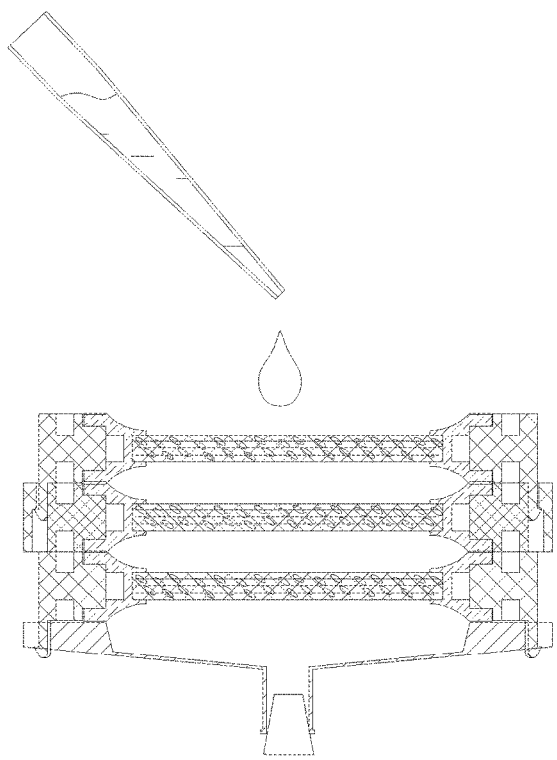
FIG. 19 is a schematic view of inoculation.
Figure 20:
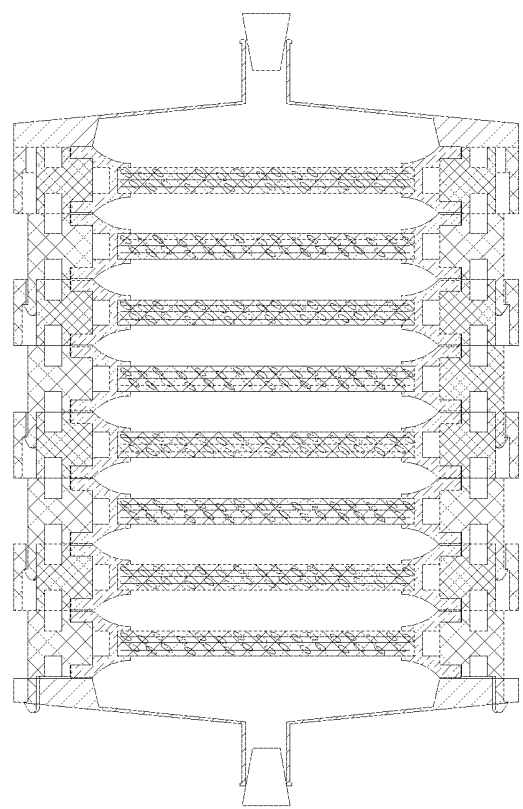
FIG. 20 is a schematic view of a single culture column.

The first tube-connecting cover was provided, and the fastening hook of the buckle ring in the above-mentioned accessory set was inserted into the mounting slot and fixed to the first tube-connecting cover through a snap fit; according to the above method, the fastening hook of the buckle ring in respective accessory set was inserted sequentially into the fastening slot of the buckle ring in another accessory set and fixed to the fixing lug boss of the buckle ring in the another accessory set through a snap fit, the sealing rings in stacked contact was pressed and fixed, and a predetermined number of scaffolds sequentially are stacked and mounted;

Cells to be cultured were inoculated onto the above mounted scaffolds, as shown in FIG. 19;

The mounting hook of the second tube-connecting cover was then inserted into the fastening slot of the buckle ring adjacent to the second tube-connecting cover, and the second tube-connecting cover was mounted and fixed, so that the culture column was assembled, as shown in FIG. 20. The culture column was placed in a $CO_2$ incubator and incubator parameters were set so that the incubator contained $CO_2$ gas at a concentration of about 5%.

2. Perfusing and Culturing Cells.

The perfusion inlet was communicated with the perfusion pump and the culture medium storage apparatus sequentially through a perfusion tube, power was provided by the perfusion pump, the culture medium in the culture medium storage apparatus was perfused into the culture column to provide nutrients for cell growth, and a metabolite produced by cell metabolism was discharged from the perfusion outlet as the culture medium flowed.

In this example, the culture medium was again introduced into the culture medium storage apparatus and recycled after it had been discharged from the perfusion outlet.

Example 2

Figure 21:
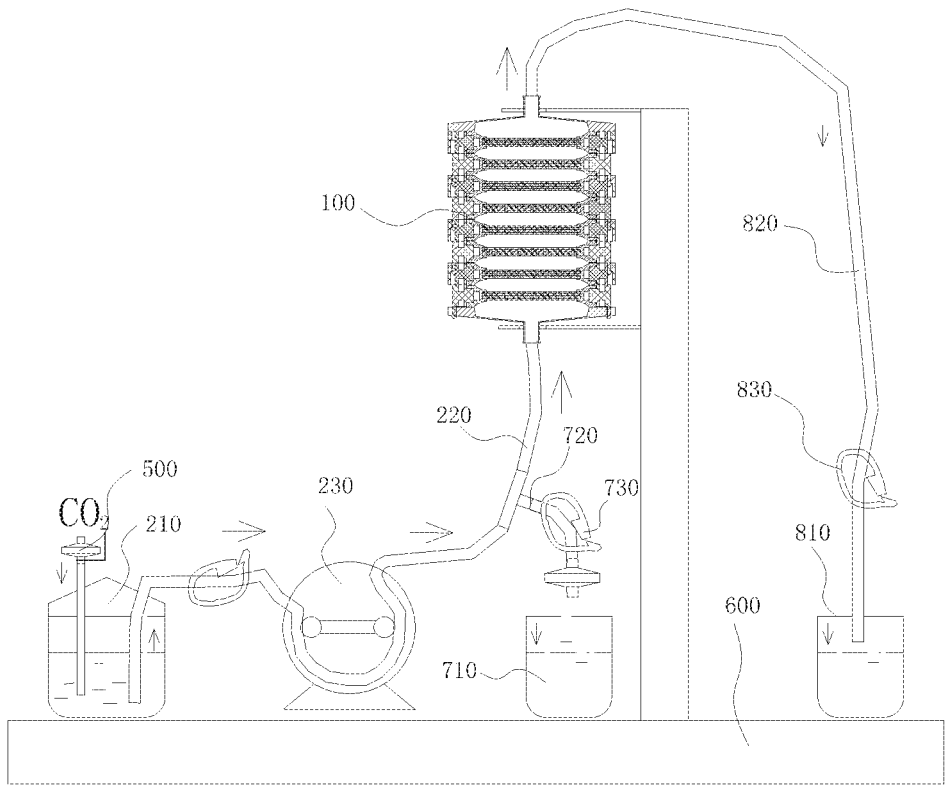
FIG. 21 is a first structural schematic view of the cell culture apparatus in Example 2.

A cell culture apparatus is as shown in FIG. 21 and substantially the same as the cell culture apparatus of Example 1, except for that:

the cell culture apparatus of this example further includes a humidification apparatus, an air filter 500, a cell harvesting bottle 710, a cell harvesting tube 720, a liquid waste bottle 810, a liquid waste tube 820, a cell harvesting valve 730, and a liquid waste valve 830.

In FIG. 21, the humidification apparatus provides humidified $CO_2$ gas into the culture medium storage apparatus 210 by humidification treatment of an culture environment in which the cell culture apparatus is located (e.g., an environment inside the cell culture incubator). Furthermore, in this example, the vent port communicating the culture medium storage apparatus 210 with the external environment is provided with an air filter 500.

It can be understood that, as shown in FIG. 22, the cell culture apparatus may further include an air pump 400, and the humidification apparatus 300, the air pump 400, and the culture medium storage apparatus 210 are sequentially communicated through a gas tube.

The cell harvesting tube 720 is communicated with the perfusion tube 220 between the perfusion pump and the perfusion inlet at one end, and is faced to the bottle opening of the cell harvesting bottle 710 at the other end. The cell harvesting valve 730 is disposed at the cell harvesting tube 720.

The waste liquid tube 820 was communicated with the perfusion outlet 121 at one end, and led into the liquid waste bottle 810 at the other end. The liquid waste valve 830 is disposed at the liquid waste tube 820.

A method for cell culture by using the above cell culture apparatus comprises the following steps:

1. Mounting the Culture Column.

The first tube-connecting cover was provided, and the fastening hook of the buckle ring in the above-mentioned accessory set was inserted into the mounting slot and fixed to the first tube-connecting cover through a snap fit; according to the above method, the fastening hook of the buckle ring in respective accessory set was inserted sequentially into the fastening slot of the buckle ring in another accessory set and fixed to the fixing lug boss of the buckle ring in the another accessory set through a snap fit, the sealing rings in stacked contact was pressed and fixed, and a predetermined number of scaffolds sequentially are stacked and mounted;

Cells to be cultured were inoculated onto the above mounted scaffolds, as shown in FIG. 19;

The mounting hook of the second tube-connecting cover was then inserted into the fastening slot of the buckle ring adjacent to the second tube-connecting cover, and the second tube-connecting cover was mounted and fixed, so that the culture column was assembled, as shown in FIG. 20. The culture column was placed in a $CO_2$ incubator and incubator parameters were set so that the incubator contained $CO_2$ gas at a concentration of about 5%.

2. Perfusing and Culturing Cells.

The humidification apparatus, the air pump and the culture medium storage apparatus were communicated through a gas tube, and the humidified gas containing $CO_2$ in the humidification apparatus was introduced into the culture medium storage apparatus by the air pump. The perfusion inlet was communicated with the perfusion pump and the culture medium storage apparatus sequentially through a perfusion tube, power was provided by the perfusion pump, the culture medium in the culture medium storage apparatus was perfused into the culture column to provide nutrients for cell growth, and a metabolite produced by cell metabolism was discharged from the perfusion outlet as the culture medium flowed and into the liquid waste bottle through the liquid waste tube.

Example 3

Figure 23:
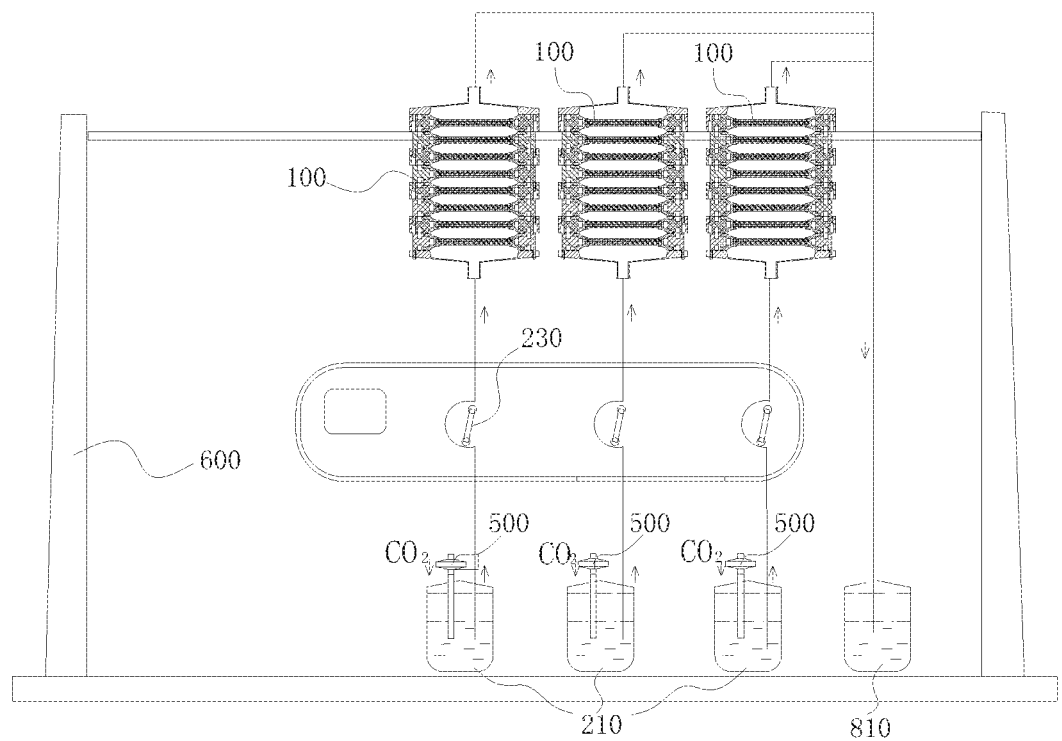
FIG. 23 is a first structural schematic view of the cell culture apparatus in Example 3.

A cell culture apparatus is as shown in FIG. 23 and substantially be same as the cell culture apparatus of Example 1, except for that:

the cell culture apparatus of this example includes three culture column 100, and further includes a humidification apparatus, an air filter 500, a liquid waste bottle 810 and a liquid waste tube 820.

In FIG. 23, the humidification apparatus provides humidified $CO_2$ gas into the culture medium storage apparatus 210 by humidification treatment of an culture environment in which the cell culture apparatus is located (e.g., an environment inside the cell culture incubator). Furthermore, in this example, the vent port communicating the culture medium storage apparatus 210 with the external environment is provided with an air filter 500.

Figure 24:
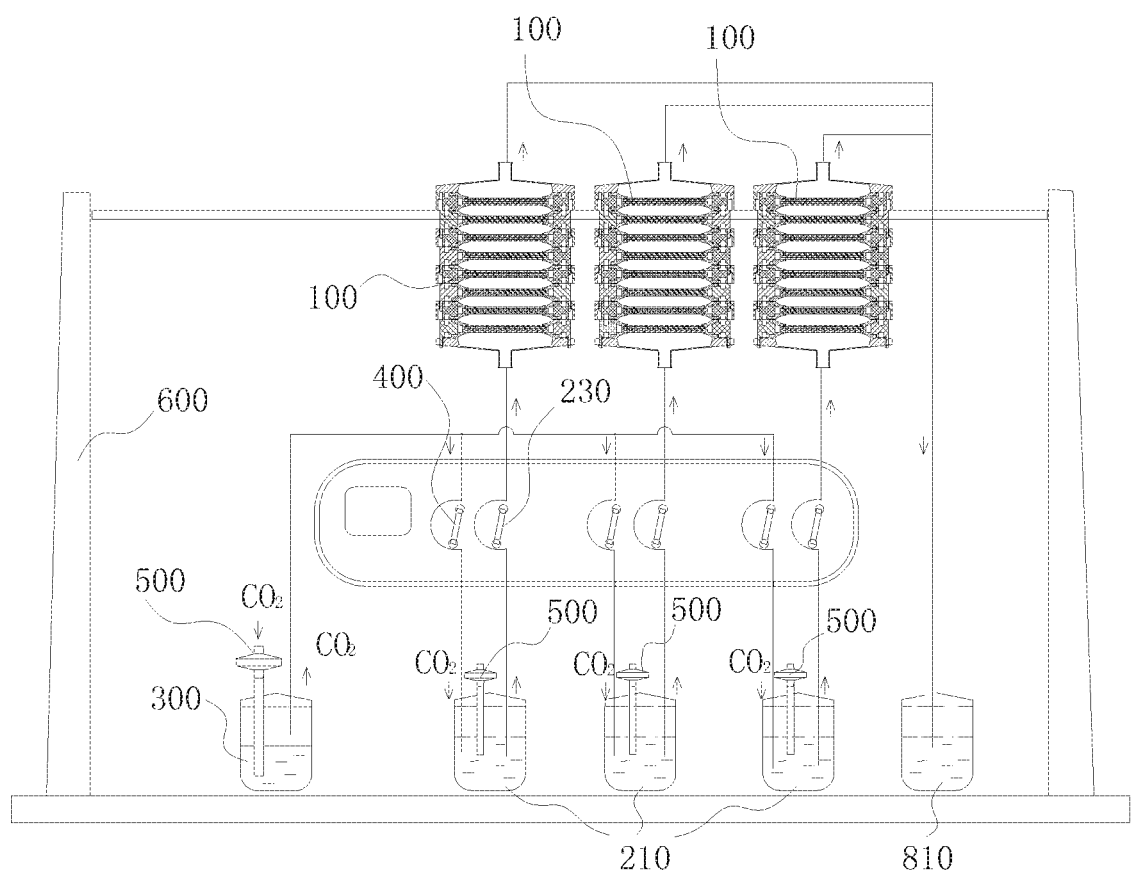
FIG. 24 is a second structural schematic view of the cell culture apparatus in Example 3.

It can be understood that, as shown in FIG. 24, the cell culture apparatus may further include an air pump 400, and the humidification apparatus 300, the air pump 400, and the culture medium storage apparatus 210 are sequentially communicated through a gas tube.

The waste liquid tube 820 was communicated with the perfusion outlet 121 at one end, and led into the liquid waste bottle 810 at the other end.

A method for cell culture by using the above cell culture apparatus comprises the following steps:

1. Mounting the Culture Column.

The first tube-connecting cover was provided, and the fastening hook of the buckle ring in the above-mentioned accessory set was inserted into the mounting slot and fixed to the first tube-connecting cover through a snap fit; according to the above method, the fastening hook of the buckle ring in respective accessory set was inserted sequentially into the fastening slot of the buckle ring in another accessory set and fixed to the fixing lug boss of the buckle ring in the another accessory set through a snap fit, the sealing rings in stacked contact was pressed and fixed, and a predetermined number of scaffolds sequentially are stacked and mounted;

Cells to be cultured were inoculated onto the above mounted scaffolds, as shown in FIG. 19;

The mounting hook of the second tube-connecting cover was then inserted into the fastening slot of the buckle ring adjacent to the second tube-connecting cover, and the second tube-connecting cover was mounted and fixed, so that the culture column was assembled.

The three culture column were assembled according to the above method, hung from and fixed to a fixing bracket.

2. Perfusing and Culturing Cells.

The humidification apparatus, the air pump and the culture medium storage apparatus were communicated through a gas tube, and the humidified gas containing $CO_2$ in the humidification apparatus was introduced into the culture medium storage apparatus by the air pump. The perfusion inlet was communicated with the perfusion pump and the culture medium storage apparatus sequentially through a perfusion tube, power was provided by the perfusion pump the culture medium in the culture medium storage apparatus was perfused into the culture column to provide nutrients for cell growth, and a metabolite produced by cell metabolism was discharged from the perfusion outlet as the culture medium flowed and into the liquid waste bottle through the liquid waste tube.

The technical features of the above-described embodiments may be combined arbitrarily. To make the description brief, all the possible combinations of the technical features in the above embodiments have not been described. However, the combination of these technical features should be considered as falling within the scope described in this specification so long as there is no contradiction.

The above-mentioned embodiments merely represent several embodiments of the present disclosure, and the description thereof is comparatively specific and detailed, but it should not be construed as limiting the scope of the disclosure. It should be noted that, for those skilled in the art, several variations and improvements may be made without departing from the concept of the present disclosure, and these are all within the protection scope of the present disclosure. Therefore, the scope of protection of the present disclosure shall be subject to the appended claims.

The invention claimed is:

1. A cell culture apparatus comprising:
a culture column including a first tube-connecting cover, a second tube-connecting cover and at least a scaffold for adherent growth of cells, the first tube-connecting cover, the at least a scaffold and the second tube-connecting cover being sequentially stacked to form a culture column having a closed cavity, and the first tube-connecting cover and the second tube-connecting cover each having a perfusion inlet and a perfusion outlet,
wherein the culture column further includes a sealing ring and a buckle ring, the sealing ring being arranged around an edge of the scaffold, the buckle ring being arranged around an edge of the sealing ring, wherein a buckle ring boss is provided in an inner circumferential side surface of the buckle ring, a buckle ring slot matching the buckle ring boss is provided in an outer circumferential side surface of the sealing ring, and the sealing rings stacked adjacently are in contact with each other; and
a perfusion system including a culture medium storage apparatus, a perfusion tube and a perfusion pump for powering perfusion, the culture medium storage apparatus, the perfusion pump and the perfusion inlet being sequentially communicated via the perfusion tube.

2. The cell culture apparatus according to claim 1, wherein at least two scaffolds are provided, and/or at least two culture columns are provided.

3. The cell culture apparatus according to claim 1, wherein the sealing ring and the buckle ring having a same number as that of the scaffold, the sealing ring being annular and arranged around an edge of the scaffold, the buckle ring being annular and arranged around an edge of the sealing ring.

4. The cell culture apparatus according to claim 1, wherein the buckle ring is further provided with a fastening hook and a fastening slot, wherein the fastening slot is provided with a fixing lug boss therein, the fastening hook may be inserted into the fastening slot of another buckle ring and fixed to the fixing lug boss of the another buckle ring through a snap-fit, and the sealing ring in a stacked contact is pressed and fixed;
the first tube-connecting cover is further provided with a mounting slot, and the fastening hook of the buckle ring adjacent to the first tube-connecting cover may be inserted into the mounting slot and fixed to the first tube-connecting cover through a snap-fit;
the second tube-connecting cover is further provided with a mounting hook, and the mounting hook may be inserted into the fastening slot of the buckle ring adjacent to the second tube-connecting cover and fixed to the fixing lug boss of the buckle ring through a snap-fit.

5. The cell culture apparatus according to claim 4, wherein the fastening hook and the fastening slot are alternately and evenly arranged around an edge of the buckle ring.

6. The cell culture apparatus according to claim 1, wherein the scaffold is formed by criss-crossing laminated fibers and a gap for cell adherent growth and circulation of the culture medium is formed between the fibers.

7. The cell culture apparatus according to claim 6, wherein a surface of the scaffold is grafted with a temperature-sensitive material, and the temperature-sensitive material is subjected to a phase change between hydrophilic phase and hydrophobic phase by changing temperature, so that the cell growing adherently to the scaffold are allowed to achieve temperature-sensitive detachment and harvested after the completion of culture.

8. The cell culture apparatus according to claim 1 further comprising a humidification apparatus and an air filter, wherein the humidification apparatus provides humidified gas for the culture medium storage apparatus; and a vent port for the culture medium storage apparatus communicating with external environment is provided with an air filter.

9. A cell culture method using the cell culture apparatus according to claim 1, comprising the following steps:
mounting the culture column: providing the first tube-connecting cover, sequentially stacking and mounting a predetermined number of scaffolds on the first tube-connecting cover, inoculating cells to be cultured onto the scaffolds, and then mounting and fixing the second tube-connecting cover on a upper portion of the scaffolds so that the culture column is assembled;
perfusing and culturing cells: communicating the perfusion inlet with the perfusion pump and the culture medium storage apparatus sequentially through the perfusion tube, providing power by the perfusion pump, perfusing a culture medium in the culture medium storage apparatus into the culture column to provide nutrients for cell growth and discharging a metabolite produced by cell metabolism from the perfusion outlet as the culture medium flows.

10. The cell culture method according to claim 9, wherein the culture column further includes a sealing ring and a buckle ring having a same number as that of the scaffold, the sealing ring being annular and arranged around an edge of the scaffold, the buckle ring being annular and arranged around an edge of the sealing ring, wherein a buckle ring boss is provided in an inner circumferential side surface of the buckle ring, a buckle ring slot matching the buckle ring boss is provided in an outer circumferential side surface of the sealing ring, and the sealing rings stacked adjacently are in contact with each other, and
wherein the step of mounting the culture column is as follow:
surrounding and sheathing the scaffold with the sealing ring, and surrounding and sheathing the sealing ring with the buckle ring to form an accessory set, and mounting several accessory sets according to the above method;

providing the first tube-connecting cover, and inserting the fastening hook of the buckle ring in the above-mentioned accessory set into the mounting slot and fixed to the first tube-connecting cover through a snap fit; according to the above method, inserting the fastening hook of the buckle ring in respective accessory set sequentially into the fastening slot of the buckle ring in another accessory set and fixed to the fixing lug boss of the buckle ring in the another accessory set through a snap fit, pressing and fixing the sealing rings in stacked contact, and stacking and mounting a predetermined number of scaffolds sequentially;

inoculating the cells to be cultured onto the above mounted scaffolds;

then, inserting the mounting hook of the second tube-connecting cover into the fastening slot of the buckle ring adjacent to the second tube-connecting cover, and mounting and fixing the second tube-connecting cover so that the culture column is assembled.

* * * * *